United States Patent [19]
Vieau

[11] Patent Number: 5,199,622
[45] Date of Patent: Apr. 6, 1993

[54] FLOSS CUTTER AND HOLDER

[76] Inventor: Robert A. Vieau, 233 Town Acres La., Roselle, Ill. 60101

[21] Appl. No.: 473,469

[22] Filed: Feb. 1, 1990

[51] Int. Cl.⁵ .................................. B65H 35/06
[52] U.S. Cl. ........................ 225/51; 225/63; 225/82
[58] Field of Search ............ 83/856; 225/51, 52, 225/63, 64, 82, 83, 84, 85; 30/290, 317, 294; 132/323, 324, 325, 326, 327

[56] References Cited

U.S. PATENT DOCUMENTS

| | | | |
|---|---|---|---|
| 752,845 | 2/1904 | Laird | 225/63 |
| 889,429 | 6/1908 | Benda | 225/63 |
| 1,044,014 | 11/1912 | Butts | 225/63 |
| 1,220,760 | 3/1917 | Leclerc | 225/63 X |
| 1,229,504 | 6/1917 | Olson | 225/63 |
| 1,926,539 | 9/1933 | Hurst | 225/64 |
| 2,145,178 | 1/1939 | Hawkins | 225/63 |
| 2,302,965 | 11/1942 | Lucia | 225/63 |
| 4,050,648 | 9/1977 | Tisma | 225/63 X |

FOREIGN PATENT DOCUMENTS 5567 of 1913 United Kingdom ................. 225/63

Primary Examiner—Douglas D. Watts
Assistant Examiner—Rinaldi Rada
Attorney, Agent, or Firm—Kinzer, Plyer, Dorn, McEachran & Jambor

[57] ABSTRACT

A device for cutting and clamping dental floss includes a cutting element and a clamping element. The cutting element has a portion thereof formed and adapted to sever dental floss when it is pulled thereacross. The clamping element is adjacent the cutting element and cooperates with it to accessibly hold the dental floss supply cut end after severing.

4 Claims, 1 Drawing Sheet

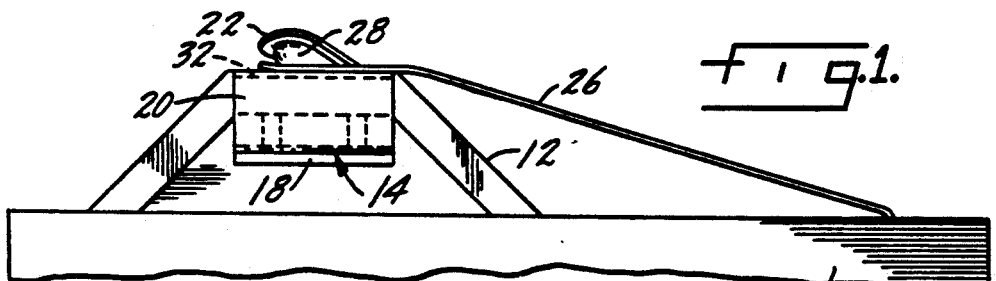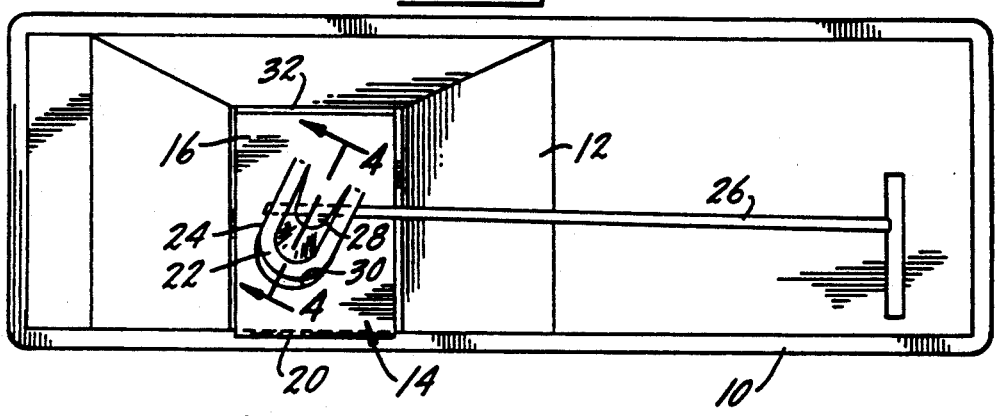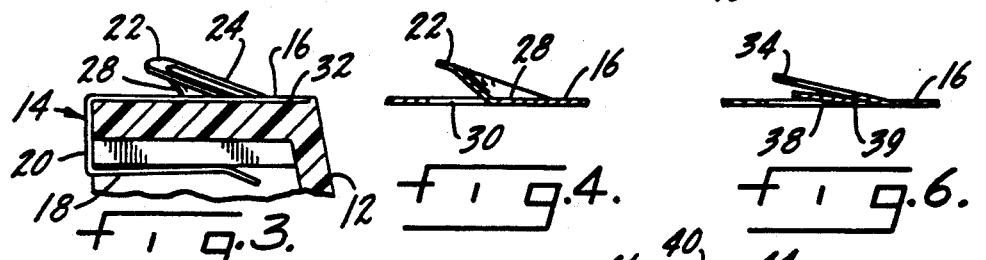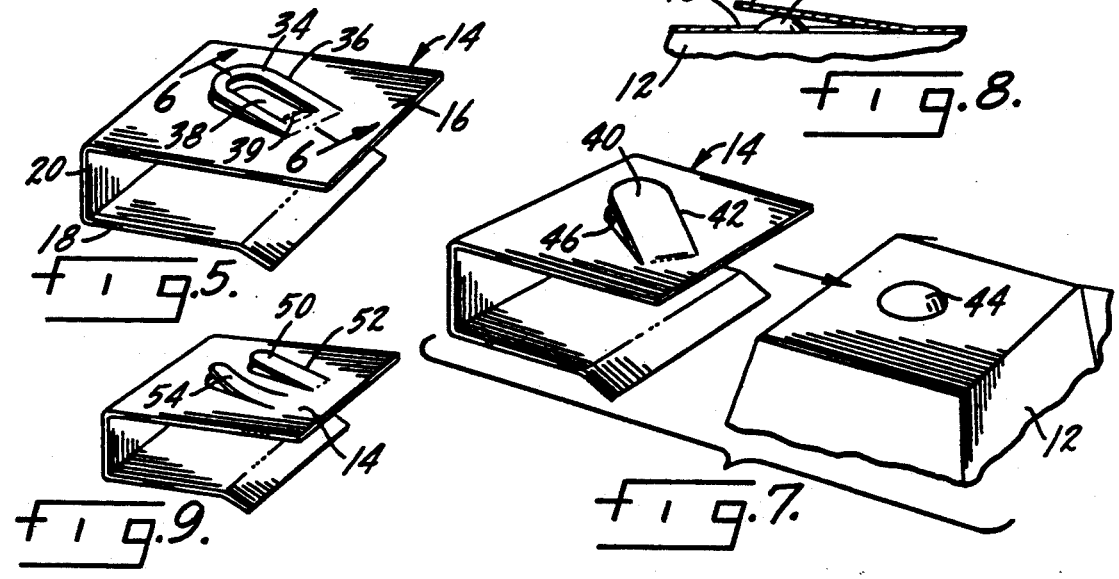

FLOSS CUTTER AND HOLDER

SUMMARY OF THE INVENTION

The present invention relates to a cutting device for severing dental floss and is particularly directed to such a device which both cuts the dental floss and clamps it after cutting, so as to maintain the accessibility of the severed end of the dental floss supply.

A primary purpose of the invention is to provide a simply constructed and reliable cutting device for use with a dental floss supply, which device insures that the severed end of the dental floss supply is clamped and available for subsequent use.

Another purpose of the invention is a cutting assembly of the type described which is removably mounted on a dental floss supply housing.

Another purpose is a device of the type described useful for mounting on a dental floss supply which both clamps and provides a cutting edge for the dental floss.

Another purpose is a dental floss cutting device as described which may be separate or integral with the dental floss supply housing.

Other purposes will appear in the ensuing specification, drawings and claims.

BRIEF DESCRIPTION OF THE DRAWINGS

The invention is illustrated diagrammatically in the following drawings wherein:

FIG. 1 is a side view of the cutting device of the present invention mounted on a dental floss supply housing, FIG. 2 is a top view of the device of FIG. 1, FIG. 3 is a partial section illustrating the cutting device of FIGS. 1 and 2, FIG. 4 is a section along plane 4—4 of FIG. 2, FIG. 5 is a perspective of a modified form of cutting device, FIG. 6 is a section along plane 6—6 of FIG. 5, FIG. 7 is an exploded perspective illustrating a further embodiment of dental floss cutting device, FIG. 8 is a partial side view of the cutting device and support of FIG. 7, and FIG. 9 is a perspective illustrating a further embodiment of the invention.

DESCRIPTION OF THE PREFERRED EMBODIMENT

Almost all known dental floss dispensers have a cutting element of one form or another. The floss is pulled out of an opening in the supply container or housing and across the cutting element, and usually a sharp pull is adequate to sever the floss. Many dental floss containers have a cover which, when closed, covers the cutting element and so protects the severed end of the dental floss supply from being accidentally retracted back through the opening. However, some dental floss containers do not have such a cover and even in those which do, the cover does not always prevent the severed end of the floss from being pulled back into the container by the supply spool. This is particularly true when the dental floss container is in a travel toilet kit and is subject to being knocked about. Most dental floss containers are of a one-piece molded plastic constructions such that if the severed end of the floss is retracted inside of the housing, there is no practical way to retrieve it and the container is thrown away and a new one purchased.

The present invention provides a dental floss cutting device which also includes an element to clamp the severed end of the floss so as to prevent it from being retracted back into the supply housing. The clamping or holding element may be integral with the cutter, it may be adjacent and related to the cutter, or it may be a separate spaced element. What is important is that there be a clamping element so that the severed end of the dental floss supply is firmly held to prevent it from being accidentally retracted into the supply housing.

In the embodiment of FIGS. 1–4, the dental floss supply housing is indicated at 10 and may conventionally be a plastic body and may have an upstanding support 12 which mounts a clip 14 which functions as the cutting device. The clip 14, a form of which is illustrated in the perspective of FIG. 5, slides over a portion of the support 12 when the clip is mounted. The clip includes a top member 16 and a bottom member 18 which is biased against a bottom wall of the support. The top and bottom are connected by a side wall 20.

In the configuration of FIGS. 1–4, cutting device or clip 14 mounts a cantilever arm 22, one edge of which, indicated at 24, functions as a cutting or severing edge. The dental floss 26 illustrated in FIG. 1 will be drawn beneath the cutting element and then sharply pulled over edge 24 to sever the floss. Clip 14 may be made of a very thin gauge metal, with the cantilever arm 22 being formed integrally with the body of the clip.

The clamping element is formed by a depression 28 which is an integral part of arm 24 and which is directly adjacent an opening 30 in the top of the clip. The lower surface of depressed portion 28, when the clip is in the assembled position shown, will be in contact with the top surface 32 of support 12.

To clamp the floss it is pulled beneath depression 28 and between the depression and the top surface 32 of support 12. Because the cantilevered arm 22 is formed of a flexible material, for example metal or perhaps plastic, the forcing of the floss beneath depression 28 and between the depression and surface 32 serves to clamp the floss in this position. The clamping force described is adequate to hold the floss, but it is not prohibitive in terms of preventing removal of the floss for subsequent use.

In the embodiment of FIGS. 5 and 6, in which like parts are given the same number, cutting device 14 has a cantilever arm 34 having a cutting edge 36 which again performs the function of cutting or severing the dental floss. In this embodiment the clamp is not a depression in the cutting arm, as shown in the embodiment of FIGS. 1–4, but rather a separate cantilever arm 38 which is cut out of the center of arm 34. A portion 39 of clamping arm 38 is bent toward support 12. The function of the cutting and clamping combination in the FIG. 5 and 6 embodiment is similar to that in FIGS. 1–4 except that it is not necessary to have a backup support surface. The floss is clamped between the underside of the clamping arm and the top member 16.

In the embodiment of FIGS. 7 and 8, clip 14 has a cantilever arm 40 with a cutting edge 42 which functions to sever or cut the dental floss. Support 12 has an upwardly extending dimple or dome 44 which extends through an opening 46 beneath cantilever arm 40, with the dome being in contact with the underside of arm 40, as illustrated particularly in FIG. 8. In use, floss will be pulled through the space between the dome and the underside of cantilever arm 40. The cutting action is the same as before. When the clip is assembled on the support, the dome 44 will extend through opening 44 a distance slightly greater than the height of the bottom of arm 40. The result is that the dome biases the cutting arm in an upward direction and this bias provides the clamping force necessary to hold the severed end of the floss between the dome and the underside of arm 40.

In the embodiment of FIG. 9, the cutter and the clamping element are separate but adjacent. Clip 14 has a cantilever cutting arm 50 having a cutting edge 52. There is a separate clamping element 54 which also is in the form of a cantilever arm which extends outwardly from the top surface of clip 14. It should be noted that the shape of the clamping element 54 is slightly different from the shape of cutting element 50 in that arm 54 is slightly concave so as to provide a more extensive clamping area. In the embodiment of FIG. 9 it is not necessary for the support 12 to provide a cooperating backup clamping surface, as clamping pressure can be derived by the interaction of the concave clamping element and the adjacent areas of the support clip.

Although the present invention discloses the cutting device as being made out of a thin spring metal, the cutting and/or clamping elements may be formed integrally with the plastic support. The invention should not be limited to any specific configuration of clamping and cutting structure, but is directed to the use of a cutting element for dental floss and an associated clamping means which cooperates with the cutting element to provide the necessary clamping force to maintain the accessibility of the floss after severing.

Whereas the preferred form of the invention has been shown and described herein, it should be realized that there may be many modifications, substitutions and alterations thereto.

The embodiments of the invention in which an exclusive property or privilege is claimed are defined as follows:

1. A device for cutting and clamping dental floss, including a body portion formed and adapted to be mounted on a housing which contains a supply of dental floss, a cantilever arm integral with and extending outwardly from said body portion and having spaced longitudinal extending edges thereof providing cutting surfaces which are formed and adapted to sever dental floss when it is pulled thereacross, a depression in said cantilever arm located generally centrally between said longitudinal edges, said depression forming a clamping element integral with said cantilever arm and having a clamping surface facing away from said cantilever arm and being formed and adapted to cooperate with a portion of the housing to accessibly hold a dental floss cut end after severing.

2. The device of claim 1 further characterized in that said body portion has a top, a bottom, and a connecting side wall, said cantilever arm being integral with said top.

3. A dental floss dispenser including a housing which contains a supply of dental floss, dental floss cutting mounted on said housing and including a body having a top, a bottom and a connecting sidewall, a cantilever arm extending outwardly from and integral with said top, said cantilever arm having spaced longitudinal cutting edges thereon providing cutting surfaces formed and adapted to sever dental floss when it is pulled thereacross, and clamping means to hold the dental floss supply cut end after severing, said clamping means including a projection extending outwardly from said housing and toward and in contact with the underside of the cantilever arm.

4. A device for cutting and clamping dental floss, including a body portion formed and adapted to be mounted on a housing which contains a supply of dental floss, a cantilever arm integral with and extending outwardly from said body portion and having spaced longitudinal cutting edges thereon providing cutting surfaces which are formed and adapted to sever dental floss when it is pulled thereacross, a cantilever clamping element formed by a cut-out portion of said cantilever arm and located generally centrally between said longitudinal edges, said cantilever clamping element having a clamping surface facing away from said cantilever arm and being formed and adapted to cooperate with a portion of the housing to accessibly hold a dental floss cut end after severing.

* * * * *